(12) United States Patent
Kroll et al.

(10) Patent No.: US 6,605,255 B2
(45) Date of Patent: Aug. 12, 2003

(54) REPINOTAN KIT

(75) Inventors: Werner Kroll, Solingen (DE); Ferdinand Rombout, Klimmen (NL); Horst Weber, Troisdorf (DE); Maria-Luisa Rodriguez, Erkrath (DE); Bernd Sennhenn, Leverkusen (DE); Rudolf Schohe-Loop, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/991,222

(22) Filed: Nov. 16, 2001

(65) Prior Publication Data

US 2003/0060493 A1 Mar. 27, 2003

(30) Foreign Application Priority Data

Nov. 22, 2000 (DE) .......................................... 100 58 119

(51) Int. Cl.$^7$ ............................ G01N 33/52; C12Q 1/00
(52) U.S. Cl. ................................. 422/61; 424/9; 435/4; 514/373; 548/210
(58) Field of Search ......................... 514/373; 548/210; 424/9; 422/61; 435/4

(56) References Cited

U.S. PATENT DOCUMENTS 5,137,901 A    8/1992    Junge et al. ................. 514/373

FOREIGN PATENT DOCUMENTS

| EP | 0352613 | 4/1994 |
| WO | 9946591 | 9/1999 |
| WO | 0109559 | 2/2001 |

*Primary Examiner*—Robert Gerstl
(74) *Attorney, Agent, or Firm*—Susan M. Pellegrino

(57) ABSTRACT

The invention relates to a kit comprising a pharmaceutical composition containing repinotan or a physiologically acceptable salt of repinotan, and a means for the determination of the concentration of repinotan or its metabolites in body fluids, and also new pharmaceutical compositions containing repinotan or a physiologically acceptable salt of repinotan, and processes for their preparation.

8 Claims, No Drawings

REPINOTAN KIT

The invention relates to a kit comprising a pharmaceutical composition containing repinotan or a physiologically acceptable salt of repinotan, and a means for the determination of the concentration of repinotan or its metabolites in body fluids, and also new pharmaceutical compositions containing repinotan or a physiologically acceptable salt of repinotan, and processes for their preparation.

For the acute treatment of neurodegenerative diseases such as stroke and cranio-cerebral trauma, which frequently lead to neurological and functional long-term deficits in these patients, up to now no treatment principle has yet been accepted worldwide as effective. Apart from the use of thrombolytics (for example t-PA) in the first 3 hours after an ischaemic stroke or the use of nimodipine in patients having a traumatic subarachnoid haemorrhage, there are still no medicinal approaches which adequately take into account the pathophysiological cascade.

EP-A-0 352 613 discloses 2-[4-({[(2R)-chroman-2-yl]methyl}amino)butyl]-1,2-benzisothiazol-3(2H)-one 1,1-dioxide (generic name: repinotan) und repinotan salts for the treatment of diseases of the central nervous system, in particular stroke.

In DE-A-195 43 476, the suitability of repinotan and its salts for the treatment of craniocerebral trauma is described.

In a number of clinical studies, repinotan has shown its good tolerability in healthy subjects and patients after a stroke or craniocerebral trauma. Moreover, the existing clinical data indicate the fact that it was possible to improve the neurological and functional deficits (after 3 and 6 months respectively depending on indication). In particular in the case of patients who reached blood plasma concentrations in the range of about 5–20 $\mu$g/l, the result of treatment was markedly better than in the patients who had received placebo.

A particularly good result of treatment can be obtained using the kit according to the invention, which comprises a pharmaceutical composition containing repinotan or a physiologically acceptable salt of repinotan and a means for the determination of the concentration of repinotan or its metabolites in body fluids.

The use of the kit according to the invention allows a medicament which, as active compound, contains repinotan in the form of the free base or of an acid addition salt to be administered and within a short time for the actual concentrations of repinotan or its metabolites to be determined in body fluids of the treated patient. Thus it is possible without a time delay and with a small outlay in terms of personnel and apparatus to perform the dose adjustments optionally necessary for an optimal therapy. The kit according to the invention therefore represents a significant advance in the acute therapy of neurodegenerative diseases, in particular of stroke and craniocerebral trauma.

The pharmaceutical compositions comprised by the kit according to the invention can be present, for example, as tablets, coated tablets, pills, granules, aerosols, syrups, emulsions, suspensions, solutions or lyophilizates which can be reconstituted to give a solution. As active compound, the pharmaceutical compositions contain repinotan or a physiologically acceptable salt of repinotan. The active compound should be present here in a concentration of approximately 0.05 to 95% by weight, preferably of approximately 0.5 to 90% by weight, of the total mixture, i.e. in amounts which are sufficient in order to achieve the dosage range indicated. In addition to the active compound, the pharmaceutical compositions additionally contain inert, non-toxic, pharmaceutically suitable excipients.

Repinotan has the following structural formula:

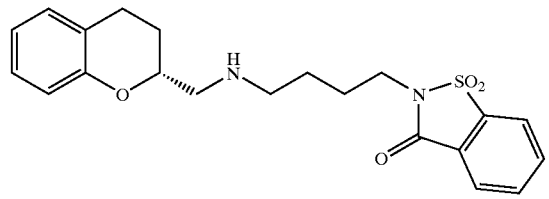

Physiologically acceptable salts of repinotan can be salts of repinotan with mineral acids, carboxylic acids or sulphonic acids. Preferred salts of repinotan are those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid. Repinotan hydrochloride is particularly preferred.

The choice of the excipients is dependent on the manner of formulation. Excipients which may be mentioned, for example, are water, non-toxic organic solvents, such as paraffins (e.g. petroleum fractions), vegetable oils (e.g. peanut/sesame oil), alcohols (e.g. ethyl alcohol, glycerol), carriers, such as, for example, ground natural minerals (e.g. kaolins, argillaceous earths, talc, chalk), ground synthetic minerals (e.g. highly disperse silicic acid, silicates), sugars (e.g. sucrose, lactose and dextrose), emulsifying agents (e.g. polyoxyethylene fatty acid esters, polyoxyethylene fatty alcohol ethers), dispersing agents (e.g. lignin sulphite waste liquors, methylcellulose, starch and polyvinylpyrrolidone) and lubricants (e.g. magnesium stearate, talc, stearic acid and sodium sulphate).

The kit according to the invention preferably comprises as pharmaceutical composition an infusion solution containing the active compound or a solid pharmaceutical composition from which this infusion solution can be prepared by addition of water or isotonic electrolyte solution.

A preferred solid pharmaceutical formulation is the lyophilizate, which can be reconstituted by addition of water or of an isotonic electrolyte solution to, for example, an infusion solution. In the lyophilizate, the active compound has an increased storage stability, and, from the lyophilizate, it is easily and rapidly possible under sterile conditions to prepare a particle-free solution which is directly suitable for use in the patient, for example as an infusion solution. In addition to the active compound, the lyophilizate advantageously contains further pharmaceutically suitable excipients, in particular matrix-forming agents.

Matrix-forming agents within the meaning of the invention are amino acids such as glycine, alanine or aspartic acid, peptides such as gelatin, collagen or albumin, monosaccharides such as glucose or lactose, disaccharides such as maltose, sucrose or trehalose, oligosacharides such as cyclodextrins or maltodextrins, polysaccharides such as starch and starch derivatives or cellulose and cellulose derivatives, polymeric matrix-forming agents such as polyvinylpyrrolidone or polyethylene glycol, salts with sodium chloride or calcium carbonate, sugar alcohols such as mannitol, sorbitol or xylitol. Mannitol, sodium chloride, glycine, sucrose, maltose and lactose are preferred. Mannitol is very particularly preferred.

If the lyophilizate is reconstituted to give an infusion solution, this is advantageously isotonic. This can be achieved by the lyophilizate already containing adequate amounts of electrolytes, such as, for example, sodium chloride, mannitol or glucose, or by an isotonic electrolyte solution being used for the reconstitution and dilution of the solution.

Isotonic electrolyte solutions are, for example, aqueous 0.9% by weight sodium chloride solutions or 5% by weight glucose solutions.

The amount of active compound in the infusion solution should be approximately 0.1 µg/ml to 1 mg/ml, preferably approximately 0.5 to 5 µg/ml.

The preparation of repinotan and repinotan salts is described in EP-A-0 352 613. Repinotan hydrochloride corresponds to Example 92H therein.

The salts according to the invention can additionally be obtained by reacting the free base repinotan in suitable solvents with stoichiometric or superstoichiometric amounts of the acid on which the salt is based in a temperature range from 0° C. up to the boiling point of the solvent. Suitable solvents are, for example, water, aliphatic alcohols such as methanol, ethanol or 2-propanol, aliphatic open-chain or cyclic ethers such as diethyl ether, tert-butyl methyl ether, dioxane, tetrahydrofuran or aliphatic ketones such as 2-propanone, 2-butanone, and also mixtures thereof. The salts are obtained directly from this mixture as a solid, optionally after partially or completely distilling off the solvent; they can be purified by recrystallization or reprecipitation in, for example, abovementioned solvents or mixtures thereof.

The pharmaceutical compositions according to the invention of the kit can also contain mixtures of repinotan and its salts or of various repinotan salts.

Repinotan or its physiologically acceptable salts can be converted in a known manner into the customary formulations, such as tablets, coated tablets, pills, granules, aerosols, syrups, emulsions, suspensions and solutions, using inert, non-toxic, pharmaceutically suitable vehicles or solvents. Preferred active compound solutions or solid pharmaceutical compositions are those which can be converted into a solution, such as, for example, lyophilizates. The therapeutically active compound here should in each case be present in a concentration of approximately 0.05 to 95% by weight, preferably of approximately 0.5 to 90% by weight, of the total mixture, i.e. in amounts which are sufficient in order to achieve the dosage range indicated.

The formulations are prepared, for example, by extending the active compounds with solvents and/or excipients, if appropriate using emulsifying agents and/or dispersing agents, where, for example, in the case of the use of water as a diluent, it is optionally possible to use organic solvents as auxiliary solvents.

The kit according to the invention moreover comprises a means for the determination of the concentration of repinotan or its metabolites in body fluids.

As analyte, it can be advantageous, instead of the active compound employed, to determine a metabolite of repinotan. Metabolites of repinotan are described.

Body fluids within the meaning of the invention are, for example, urine, blood and fractions obtained from blood, such as serum or plasma. Blood and fractions obtained from blood are preferred, particularly preferably blood plasma.

The concentration of repinotan is determined in blood or in fractions obtained from blood, preferably in blood plasma.

Suitable agents for determination of the concentration are, for example, chromatographic apparatuses such as liquid or gas chromatography, which can optionally be coupled to a mass spectrometer (LC-MS or GC-MS). Means are likewise suitable which operate according to immunological methods, such as, for example, ELISAs (enzyme-linked immunosorbent assays). Means of this type are known.

Particularly suitable means are those which can be employed at the site of treatment (bedside or point-of-care tests), since with these the dose adjustments optionally necessary for an optimal therapy can be performed without a time delay.

Preferred means in the kit according to the invention are the apparatuses for the determination of the concentration of analytes disclosed in WO-A-99/46591. These apparatuses can be produced and used according to the processes described there and allow, without a time delay and with a small outlay in terms of personnel and apparatus, the dose adjustments optionally necessary for an optimal therapy to be performed.

The kit according to the invention is particularly suitable for the acute treatment of neurodegenerative diseases, in particular stroke or craniocerebral trauma.

The pharmaceutical composition according to the invention is administered in a customary manner, preferably orally or parenterally, in particular perlingually or intravenously. In the case of oral administration, apart from the excipients mentioned, tablets, of course, can also contain additives, such as sodium citrate, calcium carbonate and dicalcium phosphate together with various additional substances, such as starch, preferably potato starch, gelatin and the like. Lubricants, such as magnesium stearate, sodium lauryl sulphate and talc can additionally be used for tabletting. In the case of aqueous suspensions, apart from the abovementioned excipients, the active compounds can be treated with various flavour enhancers or colourants. In the case of parenteral administration, solutions of the active compounds can be employed using suitable liquid carrier materials.

In general, it has proved advantageous in the case of intravenous administration to administer the active compound in amounts of approximately 0.01 µg/kg/h to 10 µg/kg/h (µg or mg per kg of body weight per hour), preferably approximately 0.05 µg/kg/h to 2 µg/kg/h to achieve effective results. The administration can in each case take place in the form of individual doses.

In the case of oral administration, the daily dose of the active compound is 0.001 to 0,2 mg/kg, preferably 10 to 100 µg/kg, of body weight.

In spite of this, if appropriate, it may be necessary to depart from the amounts mentioned, namely depending on the body weight or the type of administration route, on the individual behaviour towards the medicament, the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these into a number of individual doses over the course of the day.

In order to stabilize the patient on the therapeutically most favourable concentration of repinotan, a defined initial dose of repinotan is administered to the patient, the concentration of repinotan is checked after fixed, previously determined times using the agent according to the invention and the further dosage is then optionally adjusted.

For example, patients are infused with a solution which contains repinotan hydrochloride at a rate of 1.25 mg of repinotan/day. After 6 hours, using the agent according to the invention it is determined whether the repinotan plasma concentration is above or below about 17 µg/l. If the repinotan plasma concentration is below the threshold concentration indicated, the infusion is continued at the rate indicated. However, if the repinotan plasma concentration exceeds the threshold concentration indicated, the infusion rate is reduced to 0.5 mg of repinotan/day. 12 hours after the start of infusion, the repinotan plasma concentration is checked a further time. Again, the infusion rate is retained if the repinotan plasma concentration is below about 17 µg/l, and reduced to 0.625 or 0.25 mg of repinotan/day if the repinotan plasma concentration exceeds about 17 µg/l. In this manner, it is possible in a maximum number of patients to keep the repinotan plasma concentration in the favourable therapeutic dose range of about 5 to 20 µg/l.

In a further aspect, the invention relates to solid pharmaceutical compositions containing repinotan or its physiologically tolerable salts, and a physiologically acceptable acid.

Surprisingly it appears that by addition of a physiologically acceptable acid the storage stability of solid pharmaceutical compositions containing repinotan or its physiologically tolerable salts is increased.

Physiologically acceptable acids within the meaning of the invention are, for example, malic acid, aspartic acid, ascorbic acid, benzoic acid, succinic acid, pyruvic acid, citric acid, fumaric acid, glutamic acid, glycolic acid, hippuric acid, maleic acid, lactic acid, sulphuric acid, sorbic acid, tartaric acid or cinnamic acid. Malic acid, pyruvic acid, citric acid, fumaric acid, maleic acid, lactic acid and tartaric acid are preferred. Citric acid and tartaric acid are particularly preferred.

The action according to the invention is in particular achieved with solid pharmaceutical compositions in which the active compound, i.e. repinotan or its physiologically tolerable salts, make up 0.01–15% by weight and the physiologically acceptable acid makes up 0.5–15% by weight of the total weight of the composition.

Solid pharmaceutical compositions containing repinotan hydrochloride and citric acid or tartaric acid are very particularly preferred here.

The solid pharmaceutical compositions according to the invention can be prepared according to customary processes.

A further aspect of the invention relates to lyophilizates containing repinotan or its physiologically tolerable salts, and a physiologically acceptable acid, the preferred active compound being repinotan hydrochloride and the acids being malic acid, pyruvic acid, citric acid, fumaric acid, maleic acid, lactic acid and tartaric acid, in particular citric acid and tartaric acid. In addition, the lyophilizates can advantageously contain pharmaceutical excipients such as, for example, the abovementioned matrix-forming agents.

For the preparation of the lyophilizate, for example, the abovementioned amounts of repinotan or repinotan salt, the physiologically acceptable acid and optionally further pharmaceutical excipients are dissolved in water and/or other suitable solvents, rendered sterile, filled into suitable containers and freeze-dried.

Suitable solvents within the meaning of the invention are, for example, glacial acetic acid or tert-butanol.

The solution can customarily be prepared at temperatures from 5 to 35° C., preferably at 20 to 25° C. Rendering the solution sterile within the meaning of the invention means the conversion of the solution into the sterile state, for example by sterile filtration through filters having a maximal pore width of 0.2 µm made of suitable filter materials such as, for example, polyether sulfone or Nylon 6.6.

Suitable containers for the freeze drying are, for example, blow-moulded glass or tubular glass bottles. The dispensing volume of the solution is between 0.2 ml and 20 ml, preferably 0.5 ml to 5 ml, particularly preferably 0.7 ml to 3.0 ml.

The solution is freeze-dried in the containers. For this, the containers with the solution are placed on precooled or non-precooled shelf plates and frozen. The subsequent main drying is carried out in vacuo at chamber pressures of 0.05 mbar to 1.8 mbar at shelf plate temperatures of −40° C. to +60° C. The after drying is carried out at chamber pressures of 1 µbar to 1.8 mbar at shelf plate temperatures of −20° C. to +70° C.

Alternatively, the freeze-drying process can be carried out by the process described in the International Application PCT/EP00/07034. The storage-stable lyophilizate of the abovementioned compositions is formed by means of the freeze drying.

The invention moreover relates to infusion solutions containing repinotan or a physiologically acceptable salt of repinotan, and one or more acids selected from the group consisting of malic acid, pyruvic acid, citric acid, fumaric acid, maleic acid, lactic acid and tartaric acid, preferably citric acid or tartaric acid.

The infusion solutions according to the invention exhibit an unexpectedly high storage stability.

An infusion solution within the meaning of the invention is a solution which contains mainly water as solvent and normally has an osmolality in the range from 250 to 500 mOsmol/kg, preferably 280 to 350 mOsmol/kg. The abovementioned osmolality of the infusion solution can be achieved in that the necessary amounts of, for example, sodium chloride, mannitol or glucose are already part of the solid pharmaceutical composition and it is reconstituted and/or diluted with water, or in that the necessary amounts of these substances are added with the reconstitution/dilution medium. The repinotan concentration of the infusion solution is usually 0.1 to 500 µg of repinotan/ml of solution, preferably 0.5 to 5 µg/ml. The infusion solution contains sufficient acid such that at 20° C. the pH is 3.5 to 5, preferably approximately 4.

Normally, these solutions are added at room temperature.

Working Examples

Example 1

Lyophilizate of a Composition Containing Repinotan Hydrochloride

A mixture of 55 mg of repinotan hydrochloride (corresponds to 50 mg of repinotan), 20 g of mannitol and 3.7 g of citric acid was made up to 1 000 ml with water. This aqueous solution was sterile-filtered through filters having a maximum pore width of 0.2 µm made of polyether sulfone and dispensed into tubular glass bottles. The dispensing volume of the solution was 1 ml.

The solution was freeze-dried in the tubular glass bottles. For this, the tubular glass bottles containing the solution at room temperature were placed on the shelf plates of the freeze dryer and frozen at −40° C. The subsequent main drying was carried out in vacuo at a chamber pressure of 0.2 mbar at a shelf plate temperature of 0° C. The after drying was carried out at a chamber pressure of 10 µbar at a shelf plate temperature of 40° C. The storage-stable final product was formed by means of the freeze drying.

Alternatively, the freeze drying can be carried out according to the process described in the International Application PCT/EP00/07034.

Analogously to the process described in Example 1, lyophilizates containing 0.27 g, 0.681 g, 1.36 g and 2.73 g of repinotan hydrochloride, corresponding to 0.25 g, 0.625 g, 1.25 g and 2.5 g respectively of repinotan were prepared with the amounts of mannitol, citric acid and water used in Example 1.

Example 2

Infusion Solution Containing Repinotan Hydrochloride

A ready-to-use infusion solution is prepared from the freeze-dried product according to Example 1 by reconstituting the lyophilizate with the aid of a 0.9% by weight NaCl solution and then diluting with this solution to a total volume of 500 ml. The ready-to-use solution is chemically stable on storage for at least 30 h at room temperature, i.e. the solution then still contains at least 90% unchanged repinotan.

Example 3

Determination of Repinotan with the Aid of an ELISA on Microtitre Plates

The test is carried out on the basis of a competitive ELISA. The protein conjugate of a hapten analogous to repinotan is reacted with a constant amount of monoclonal or polyclonal antibody Fab or Fab2 fragment, specifically against the chemical structure of repinotan, and a constant volume of repinotan-containing sample. From the ratio of bound to free protein conjugate, it is then possible to determine the concentration of repinotan by means of a calibration curve to be plotted in parallel using known concentrations of repinotan in the sample to be investigated.

Goat IgG is chemically linked to the repinotan analogues mentioned below in the molar ratio 1:7.5. This conjugate is incubated in a 0.1 M sodium carbonate buffer pH=9.6 for 1 h at 37° C. in a microtitre plate (e.g. Dynex Immulon 2HB). It is then blocked for 30 min at room temperature using a phosphate-buffered, casein-containing (1%) saline solution. Subsequently, it is washed three times with Tween-containing (0.05%) phosphate-buffered saline solution.

The competitive test can now be carried out on the plate prepared in this way. For this, 100 $\mu$l of sample are introduced into a microtitre well and treated with 100 $\mu$l of antibody solution (mouse anti-repinotan antibody 10 ng/ml in phosphate-buffered saline solution). The mixture is incubated at room temperature for 1 h. After washing three times with wash buffer (see above), in a further reaction secondary antibody, coupled to horseradish peroxidase (1:1; Zymed goat-anti-mouse IgG; diluted 1:1 000), is pipetted into the microtitre well. This binds to the repinotan-specific mouse antibody which is bound to the repinotan-analogous hapten conjugate. The amount of repinotan-specific mouse antibody bound in this way is indirectly proportional to the amount of free repinotan in the sample. By washing three times, excess antibody-enzyme conjugate is washed off and, after addition of enzyme substrate (TMB), the remaining amount bound is determined photometrically by means of kinetic measurement. Using the protocol shown, repinotan concentrations of between 1 and 100 ng/ml can be determined using appropriate calibrators.

Example 4

Point-of-care Repinotan Test

This repinotan test is intended for use in the area of intensive care and other hospital areas for the determination of repinotan concentrations above and below a defined threshold concentration of approximately 17 ng/ml in whole blood, serum or plasma. This is a once-off test having a visual readout.

Description of the Apparatus

The test is based on the competitive immunological process for the determination of small molecules described above. As a read-out mechanism, instead of an enzymatic spectroscopic process, the reflective signal from colloidal gold particles is used. All necessary test components and mechanical manipulations which are necessary for carrying out conventional immunoassays are incorporated into a plastic device. This contains a mechanism for the separation of the blood cells from the serum and a mechanism for the exact measuring out of a certain amount of the serum separated in this way. A buffer reservoir contains the liquid phase necessary for the reaction, which makes possible the capillary motion within the system. Anti-repinotan antibody and hapten-goat IgG-gold conjugate are lyophilized in a reaction cell of the plastic device. A mixing chamber at the end of a capillary and an immunochromatographic test strip complete the system. Stationary reaction zones are applied to the test strips: a donkey anti-mouse antibody and a rabbit anti-goat antibody.

In the absence of repinotan, the donkey anti-mouse antibody traps the predominant part of the gold conjugate and forms a red colour zone. With increasing repinotan concentration in the sample to be investigated, the gold conjugate displaced proportionally to the anti-repinotan antibody is trapped in the rabbit anti-goat reaction.

At the end of the immunochromatographic test strip is an absorption zone at whose beginning a water-soluble dye is applied. This dye moves forward with the liquid front and moves it to the end of the absorption zone. This indicates the end of the test reactions.

The duration of the test is about 15 min, from the application of the sample to the reading off of the result. The test can be carried out with 100–150 $\mu$l of whole blood, which guarantees the generation of about 15 $\mu$l of serum.

The following reaction components are needed for the preparation of the test device:

a) monoclonal anti-repinotan
b) gold-repinotan analogue-goat IgG conjugate
c) colloidal gold, 20 nm
d) nitrocellulose membrane
e) goat anti-mouse
f) rabbit anti-goat
g) repinotan standard
h) 0.2% Triton X 305 in phosphate-buffered saline assay buffer
i) 0.4% Nonidet P-40, 2% BSA, 2.5% sucrose, 1.25% trehalose, in phosphate-buffered saline lyophilized buffer
j) 2.5 cm sink material
k) plastic backing, 5.3 cm wide and 8 mil. thick
l) human serum Test Procedure About 150 $\mu$l of whole blood (5 drops), serum or plasma are applied to the sample plate. The device is stored in the horizontal position for about 3 minutes. The handle of the addition flask is then rotated by 90° until it lies flat on the bottom of the device. The device is then stored at room temperature in the horizontal position for 15 min. When a blue point appears at the indicator window, the test is concluded and the results can be read off.

Apart from the sample application and the operation of the addition flask, no further manipulations of the sample or of the device are necessary for the entire carrying-out of the test. The test can therefore also be carried out by non-technical personnel.

Interpretation Result

As described in WO-A-99/46591, the comparison of the intensity of the two bands in the windows A and B allows the simple semi-quantitative determination of the repinotan concentration. If the signal in window A is more intense than that in window B, the repinotan concentration is above a certain threshold value, in the case of the reverse intensity distribution below a certain threshold value. The threshold value can be established by means of the ratio of the anti-repinotan antibody concentration and the concentration of the gold-repinotan analogous goat IgGs in the lyophilizate.

The repinotan analogue in the gold-repinotan analogue-goat IgG conjugate is a compound of the formula:

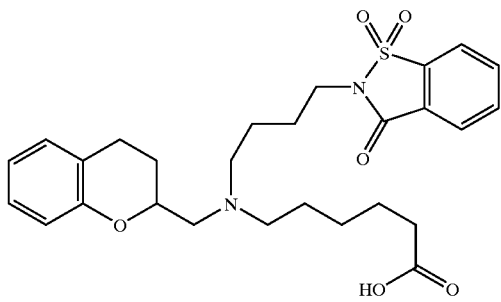

This compound is new and can be prepared according to the process described in EP-A-0 352 613, for example by reaction of repinotan with tertiary-butyl 6-bromo-hexanecarboxylate in the presence of a base in suitable solvents and subsequent acidic ester cleavage.

What is claimed is:

1. Kit comprising
   a) a pharmaceutical composition containing at least one of
      i) repinotan and ii) a physiologically acceptable salt of repinotan, and
   b) means for determining the concentration of repinotan or its metabolites in body fluids.

2. Kit according to claim 1, where the pharmaceutical composition contains repinotan hydrochloride.

3. Kit according to claim 1 or 2, where the determination means operates on blood or fractions obtained from blood as said bodily fluids.

4. Kit according to claim 3, where the determination means operates on blood plasma, a fraction obtained from blood.

5. Kit according to claim 1, where the determination means operates according to an immunological process.

6. Kit according to claim 1, where the determination means can be employed at the site of treatment.

7. A method for determining the concentration of repinotan or its metabolites in body fluids as an aspect of the acute treatment of neurodegenerative diseases, comprising employing the kit of claim 1.

8. A method for determining the concentration of repinotan or its metabolites in body fluids as an aspect of the acute treatment of stroke or craniocerebral trauma, comprising employing the Kit of claim 1.

* * * * *